(12) United States Patent
Tanzman

(10) Patent No.: US 11,980,241 B2
(45) Date of Patent: May 14, 2024

(54) ARTICLES OF APPAREL

(71) Applicant: Tommie Copper IP, Inc., Mount Kisco, NY (US)

(72) Inventor: Christina Tanzman, Brewster, NY (US)

(73) Assignee: Tommie Copper IP, Inc., Mount Kisco, NY (US)

( * ) Notice: Subject to any disclaimer, the term of this patent is extended or adjusted under 35 U.S.C. 154(b) by 601 days.

(21) Appl. No.: 16/442,333

(22) Filed: Jun. 14, 2019

(65) Prior Publication Data

US 2019/0380408 A1     Dec. 19, 2019

Related U.S. Application Data

(60) Provisional application No. 62/685,624, filed on Jun. 15, 2018.

(51) Int. Cl.
| | |
|---|---|
| A41D 31/00 | (2019.01) |
| A41B 1/08 | (2006.01) |
| A41D 13/00 | (2006.01) |

(52) U.S. Cl.
CPC ............ *A41D 31/0005* (2013.01); *A41B 1/08* (2013.01); *A41D 13/0015* (2013.01); *A41D 2400/38* (2013.01)

(58) Field of Classification Search
CPC ............... A41D 13/0015; A41D 31/18; A41D 31/0005; A41D 2400/38; A41D 31/00; A41D 27/24; A41D 31/185; A41D 31/04; A41D 1/04; A41D 13/00; A41D 13/02; A41D 3/00; A41D 3/005; A41D 7/00; A41D 2600/00; A41D 2600/10;
(Continued)

(56) References Cited

U.S. PATENT DOCUMENTS 3,116,735 A     1/1964  Geimer
5,839,122 A  *  11/1998 Dicker ............... A63B 21/4025
                                                  2/69
(Continued)

FOREIGN PATENT DOCUMENTS

JP          3183828 U      5/2013
KR    1020170044920 A      4/2017
(Continued)

OTHER PUBLICATIONS

TommieCopper—Men's Pro-Grade Shoulder Centric Support Shirt; https://www.tommiecopper.com/mens-shoulder-shirt, accessed on Apr. 3, 2018.
(Continued)

*Primary Examiner* — Bao-Thieu L Nguyen
*Assistant Examiner* — Uyen T Nguyen
(74) *Attorney, Agent, or Firm* — Locke Lord LLP; Gabrielle L. Gelozin

(57) ABSTRACT

A garment comprising a plurality of panels connected to one another at respective seams. The plurality of panels includes a front panel and a center back section opposite from the front panel. The center back section defines a center panel axis that is co-axial with a center axis of the garment. A shoulder panel extends between the front panel and the center back section, wherein the shoulder panel is configured and adapted to support and pull back a wearer's shoulders.

11 Claims, 13 Drawing Sheets

(58) Field of Classification Search
CPC .. A41D 2300/22; A41B 1/08; A42D 2400/32; A42D 2400/00
USPC .............................................................. 2/69
See application file for complete search history.

(56) References Cited

U.S. PATENT DOCUMENTS

| | | | |
|---|---|---|---|
| 6,353,934 B1* | 3/2002 | Tada ...................... | A41D 27/10 2/87 |
| 8,047,893 B2 | 11/2011 | Fenske | |
| 8,375,468 B2 | 2/2013 | Okamoto et al. | |
| 8,533,864 B1* | 9/2013 | Kostrzewski ...... | A41D 13/0015 2/69 |
| 8,556,840 B2 | 10/2013 | Burke et al. | |
| 9,125,442 B2 | 9/2015 | Brown | |
| 9,226,534 B2 | 1/2016 | Puni | |
| 9,655,389 B2 | 5/2017 | Blakely | |
| 9,883,703 B2 | 2/2018 | Schultz | |
| D812,848 S | 3/2018 | Chiang et al. | |
| D812,849 S | 3/2018 | Chiang et al. | |
| 2009/0113596 A1* | 5/2009 | Young ...................... | A41D 1/00 602/61 |
| 2010/0256717 A1* | 10/2010 | Brown ............... | A41D 13/0015 607/115 |
| 2010/0299799 A1* | 12/2010 | Belluye .............. | A41D 13/0015 2/243.1 |
| 2012/0150085 A1 | 6/2012 | Kayser | |
| 2013/0104280 A1* | 5/2013 | Boynton ................. | A61F 5/026 2/69 |
| 2014/0148741 A1* | 5/2014 | Moran ................... | A41D 31/18 601/84 |
| 2014/0196190 A1* | 7/2014 | Brown ................. | A41C 3/0057 2/69 |
| 2014/0336556 A1 | 11/2014 | Pucik | |
| 2015/0040286 A1* | 2/2015 | Schultz .................... | A41D 1/00 2/88 |
| 2017/0027240 A1* | 2/2017 | McClean ................. | A41D 1/14 |
| 2017/0216077 A1 | 8/2017 | Chahrour | |
| 2017/0231798 A1 | 8/2017 | Shin | |

FOREIGN PATENT DOCUMENTS

| | | |
|---|---|---|
| WO | WO-2013138468 A1 | 9/2013 |
| WO | WO-2016128710 A1 | 8/2016 |
| WO | WO-2016165951 A1 | 10/2016 |
| WO | WO-2016185029 A1 | 11/2016 |

OTHER PUBLICATIONS

Intelliskin—Foundation Pro Series—For the High Performance Lifestyle, https://www.intelliskin.net/?gclid=EAIalQobChMI08r1556e2glVCLjACh2RlgTNEAAYASAAEgKVFvD_BwE, accessed on Apr. 3, 2018.

AlignMed—Posture Shirt, https://alignmed.com/, accessed on Apr. 3, 2018.

* cited by examiner

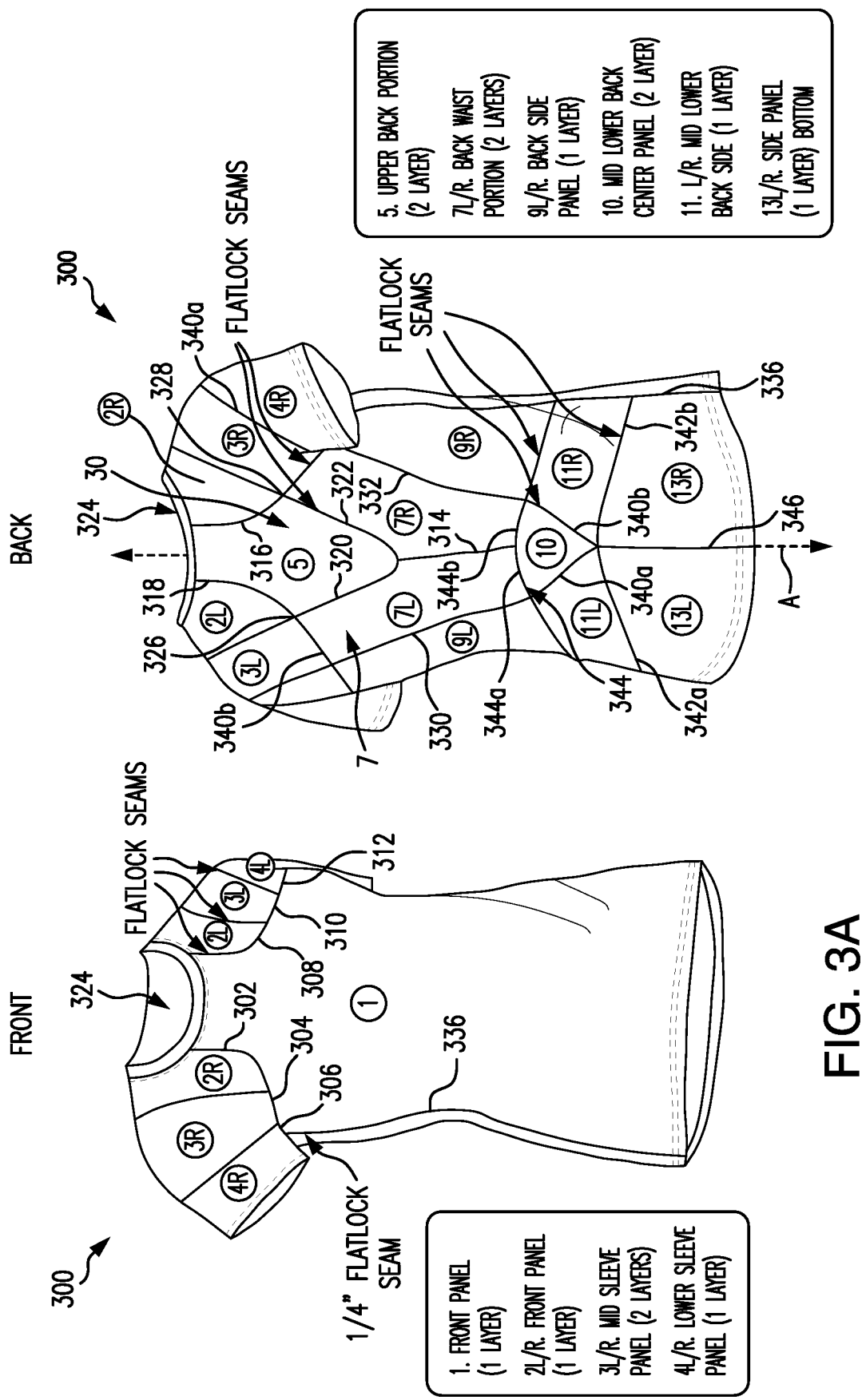

FLATLOCK

2 Layer Lapped Seam

4 Layer Lapped Seam

ARTICLES OF APPAREL

CROSS-REFERENCE TO RELATED APPLICATIONS

The subject application claims the benefit of priority to U.S. Provisional Patent Application No. 62/685,624, filed Jun. 15, 2018, the contents of which are incorporated herein by reference in their entirety.

BACKGROUND

1. Field

The present disclosure relates to apparel, and more particularly to garments for posture support.

2. Description of Related Art

Good posture is preferred in order to promote back health and comfort. Poor posture can cause a variety of health problems, such as lower back pain and/or neck pain. Good posture is desired in a variety of physical states, e.g. standing, sitting, walking and/or running. Various articles of clothing are known for use as torso garments, e.g. such as shirts used for the upper torso. Some of these shirts include compression material that may provide support for the upper torso.

The conventional techniques have been considered satisfactory for their intended purpose. However, there is an ever present need for improved shirts. This disclosure provides a solution for this need.

SUMMARY

A garment comprising a plurality of panels connected to one another at respective seams. The plurality of panels includes a front panel and a center back section opposite from the front panel. The center back section defines a center panel axis that is co-axial with a center axis of the garment. A shoulder panel extends between the front panel and the center back section, wherein the shoulder panel is configured and adapted to support and pull back a wearer's shoulders.

In some embodiments, the center back section includes a unitary central back panel. The unitary central back panel can have an upper back portion and a waist portion. The upper back portion and the waist portion can have a first modulus of elasticity and wherein the shoulder panel can have a second modulus of elasticity. The second modulus of elasticity can be greater than the first modulus of elasticity. The center back section can include a waist panel that is angled relative to the center panel axis. The waist panel and the shoulder panel can each have the same modulus of elasticity. The waist portion can be angled relative to the center panel axis. The waist portion, the upper back portion and the shoulder panel can have moduli of elasticity greater than remaining portions of the garment. The waist portion can include a top edge that abuts and connects to the shoulder panel at a bottom edge of the shoulder panel to provide targeted compression at a shoulder and muscles along a spine and to retract a wearer's shoulder blades. A connection between the waist portion and the shoulder panel can be proximate to a shoulder blade region of a wearer. The central back panel can include two layers of fabric.

In some embodiments, the waist portion includes first and second sub-portions. The first and second sub-portions can be symmetrical about the center panel axis and abut one another along the center panel axis to form a v-shape. The center back section can include a waist panel that is angled relative to the center panel axis. The plurality of panels can include a lower back panel connected to a lower edge of the center back section. The lower back panel can extend from the lower edge of the center back section to a bottom seam of the garment.

At least one of the plurality of panels can be cut approximately 8-14% shorter than an intended coverage area to stretch when worn and assist in lifting and pulling back of at least one shoulder. A fabric grain of the center back section can be aligned with the center panel axis. A fabric grain of the shoulder panel can be angled with respect to the center panel axis. At least one of the center back section or the shoulder panel can include two layers of fabric. The center back section can include a waist panel and an upper back panel. The waist panel and the upper back panel each can include two layers of fabric. The shoulder panel can extend in a posterior direction from the front panel. The shoulder panel can be connected to the center back section at a respective seam.

In accordance with another aspect, a method for making a garment includes cutting one or more of a plurality of panels from at least one fabric panel with a grain of the fabric panel. The plurality of panels include a front panel, a central back panel defining a center panel axis that is co-axial with a center axis of the garment, and a shoulder panel extending between the front panel and the central back panel. The shoulder panel is configured and adapted to support and pull back a wearer's shoulders. The method includes connecting the plurality of panels to one another at respective seams.

These and other features of the systems and methods of the subject disclosure will become more readily apparent to those skilled in the art from the following detailed description of the preferred embodiments taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein:

FIG. 3A is a perspective view of another embodiment of a garment for an upper torso portion constructed in accordance with the present disclosure, showing the garment a front side;

FIG. 4A is a perspective view of the garment of FIG. 3A, showing the garment from a back side;

DETAILED DESCRIPTION

Figure 1A:
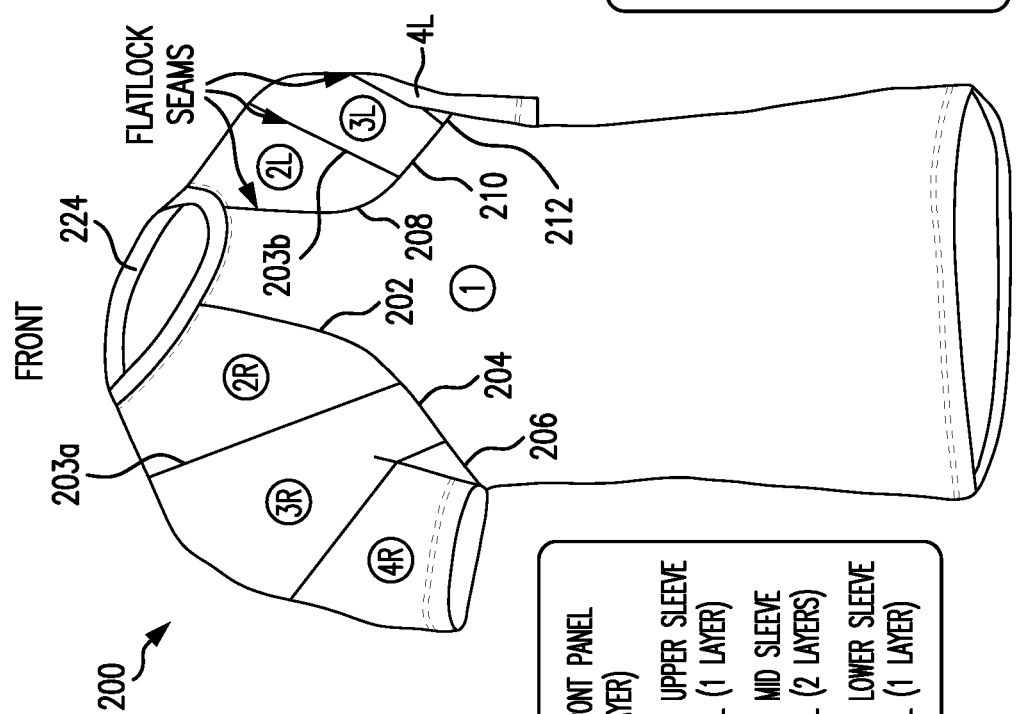
FIG. 1A is a perspective view of an embodiment of a garment for an upper torso portion constructed in accordance with the present disclosure, showing the garment from a front side.

Reference will now be made to the drawings wherein like reference numerals identify similar structural features or aspects of the subject disclosure. For purposes of explanation and illustration, and not limitation, a partial view of an exemplary embodiment of garment in accordance with the disclosure is shown in FIG. 1A and is designated generally by reference character 200. Other embodiments of garments in accordance with the disclosure, or aspects thereof, are provided in FIGS. 2A-11B, as will be described. The garments described herein can be used to support and pull pack a wearer/user's shoulders by providing targeted compression at the shoulders and muscles along the spine and retracting your shoulder blades to help relieve everyday aches and pains, while encouraging an upright, healthy posture.

As shown in FIGS. 1A-2B, garment 200 is a shirt that includes a plurality of panels connected to one another at respective seams to enclose an interior space that can be filled by a user/wearer of the shirt. A front panel 1 largely makes up the front (anterior) portion of garment 200 and is connected to a plurality of shoulder/sleeve panels. Garment 200 includes shoulder panels, e.g. mid shoulder/sleeve panels 3R/3L and upper sleeve/shoulder panels 2R/2L, that extend from a front side of the garment, over the shoulder to a back side of the garment. Mid shoulder panel 3R and upper sleeve panel 2R are connected to one another at a respective shoulder seam 203a that extends from a front side of the shirt to a back side. In some embodiments, it is contemplated that mid shoulder panels and upper sleeve panels can be a single panel, e.g. panels 3R and 2R can be a single unitary panel and panels 3L and 2L can be a single unitary panel. Garment 200 includes a unitary central back panel 30 which includes an upper back portion 5 and a waist portion 7 that are different portions of a single central back panel 30. Central back panel 30 and its portions 5 and 7 are aligned along a center axis A of the back side of garment 200, e.g. such that a center axis of each portion is co-axial with center axis A. Each of the back panel portions 5 and/or 7 are connected to at least one of the shoulder panels, e.g. mid shoulder/sleeve panels 3R/3L, at respective seams (240a and/or 240b, described below) to support and pull back a wearer's shoulders to promote healthy posture. Waist portion 7 includes waist sub-portions 7R and 7L. In the embodiment of FIG. 1B, waist portion 7 and upper back portion 5 are referred to together as a center back section.

As shown in FIG. 1A, front panel 1 is connected to an upper right sleeve panel 2R along a first front panel seam 202. Front panel 1 is connected to a mid-shoulder panel 3R along a second front panel seam 204. Front panel 1 is connected to a right sleeve panel 4R along a third front panel seam 206. Front panel 1 is connected to an upper left sleeve panel 2L along a fourth front panel seam 208. Front panel 1 is connected to a mid-sleeve panel 3L along a fifth front panel seam 210. Front panel 1 is connected to a right sleeve panel 4R along a sixth front panel seam 212. Right and left lower sleeve panels 4R and 4L, respectively, each include one fabric layer. Seams 202, 204 and 206 can be a single continuous seam. Seams 208, 210 and 212 can also be a single continuous seam.

Figure 2A:
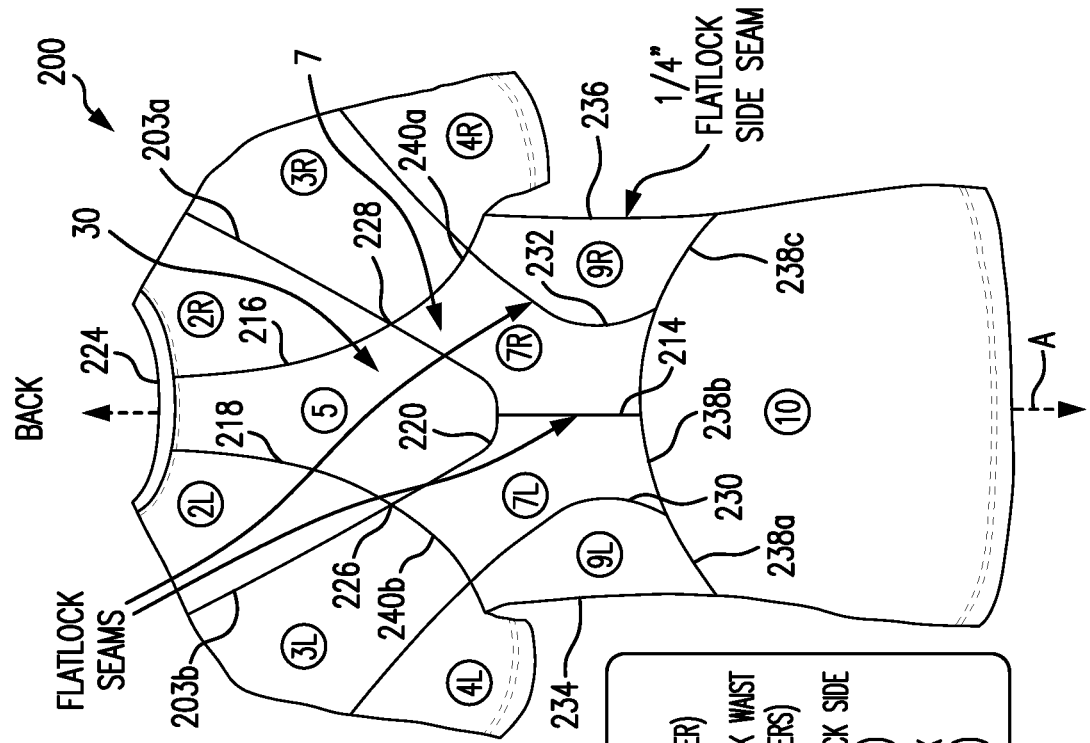
FIG. 2A is a perspective view of the garment of FIG. 1A, showing the garment from a back side.

With continued reference to FIGS. 1A and 2A, panels 2L and 2R extend from the front side to the back side of the garment over a region proximate to upper shoulder of the user. Panels 3L and 3R extend from the front side to the back side of the garment over a region proximate to the middle of the shoulder of the user. Panels 4L and 4R extend from the front side to the backside of the garment over a region proximate to the lower shoulder and upper arm of the user. Panels 4L and 4R each form a respective sleeve. Those skilled in the art will readily appreciate that panels 4L and 4R are optional, and in other embodiments of the invention, such as tank-tops, sports bras, or the like, they may not be present. Moreover, left and right mid shoulder panels 3L and 3R, may be truncated to accommodate for embodiments of the invention incorporated into tank-tops, sports bras, or the like. In some embodiments, such as garments 400 and 500, shown in FIGS. 10A-11B, panels 4L and 4R may extend to a wrist region on a user to be a long-sleeve garment. The other panels (other than 4L and 4R) of embodiments 400 and 500 are the same as those of garments 200 and 300, respectively.

As shown in FIGS. 1A-1B and 2A-2B, left and right mid shoulder panels 3L and 3R, respectively, are cut with the grain of the fabric to limit the stretch of the panels in the downward direction as oriented in FIGS. 1A-1B and 2A-2B. The direction of the grain is schematically by double headed arrows of FIGS. 1B and 2B. Left and right mid shoulder panels 3L and 3R, respectively, are cut 8-14% shorter (in all directions) than the intended coverage area and then stretched and connected to abutting panels in tension. When worn, this creates vertical motion that results in the panels 3R and 3L (in conjunction with portions 7R and 7L described below) to pull the shoulders back, encouraging an enhanced shoulder position and healthy posture. It is contemplated that other panels described herein can also be cut short of the intended coverage area on all sides (e.g. in the vertical and horizontal direction), so the shirt provides over all compression and stays in place on the user. For example, if a women's "small chest" measurement should be between 34-36 inches, the torso is of the garment is cut to 28 inches—an eight inch difference in circumference and four inches per flat side. In other words, flat front panel 1 would be cut four inches less than that to create a pull/compression and the back panels would be cut to an equivalent difference to result in the eight inch total reduction. Left and right mid shoulder panels 3L and 3R also provide targeted compression proximate to a mid-shoulder region of the user. Right and left mid shoulder panels 3R and 3L, respectively, each include two fabric layers. Having two fabric layers for panels 3L and 3R provide additional support and assist in enhancing the pulling effect described below, with respect to waist portion 7. Panels 3L and 3R are mirror images of one another. In some embodiments, both panels 3L and 3R are approximately four inches wide at their respective longitudinal mid-points. The longitudinal mid-points of panels 3L and 3R approximately correspond to the top of a wearer's shoulder. This width enables panels 3L and 3R to cover the majority if not all of their respective shoulder joints, which when vertical pressure/movement is applied to effectively pulls back each shoulder. Panels 3L and 3R start from respective front armhole seams 210 and 204 and extend in a posterior direction toward the back side of garment 200 over the shoulder joint to the shoulder blade where they join with back waist portion 7 of back panel 30 at respective seams 240a and 240b.

Figure 2B:
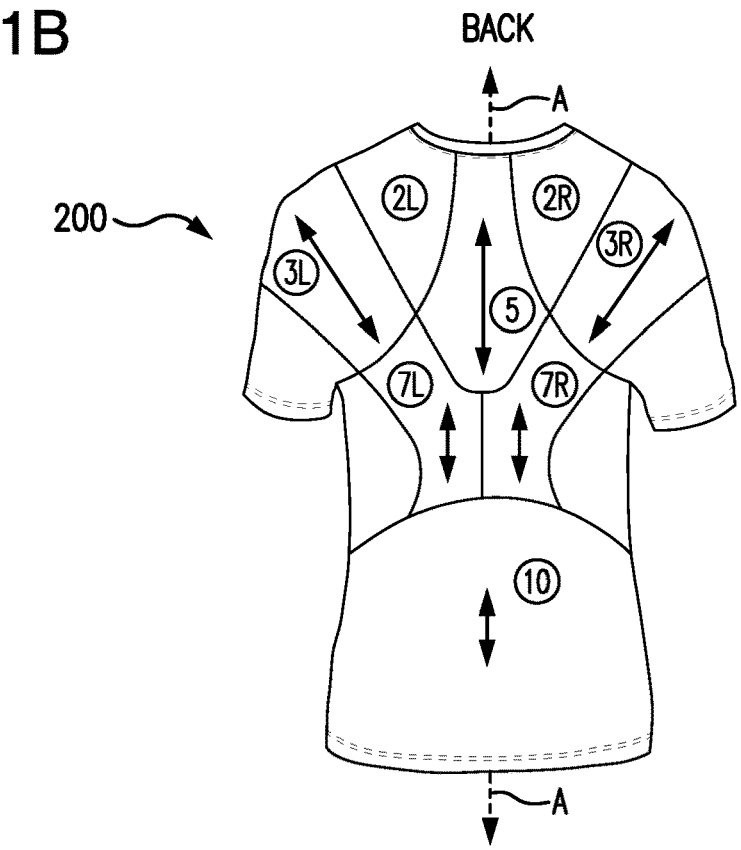
FIG. 2B is a perspective view of the garment of FIG. 2A, schematically showing the grain direction of the fabric for some of the panels with double-headed arrows.

With reference now to FIG. 2A-2B, back waist portion 7 (along with upper back portion 5) is part of single back panel 30 in the plane of the paper in FIG. 2A, but includes two layers of fabric. Portion 7 includes right and left back waist sub-portions 7R and 7L, respectively. Right and left back sub-portions 7R and 7L are separated by a center seam 214. Center seam 214, however, is a quasi-faux seam because sub-portions 7R and 7L are already part of the same panel. Center seam 214 does, however, connect the two layers of fabric panel 30 (in a direction in and out of the page as oriented in FIG. 2A), which acts to keep the layers of central back panel 30 from moving around relative to one another. Back waist portion 7 is cut with the grain of the fabric to limit the stretch of the panels in the downward direction toward the mid lower back center panel 10. The grain direction of the fabric for waist portion 7 is shown in FIG. 2B. Panels 3R and 3L and sub-portions 7L and 7R of center panel 30 are designed to be 8-14% shorter than the intended coverage area in all directions. These joined diagonal shorter panels/portions 3R, 3L, 7R and 7L are the ones that create force to "pull back" the shoulders of a wearer. Waist portion 7 is connected to right mid shoulder panel 3R at respective seam 240a and waist portion 7 is connected to left mid shoulder panel 3L at respective seam 240b. When worn, the connection between waist portion 7 and panels 3R and 3L creates a pulling/stretching effect due to the difference between the length of panel 30 (at rest) and the intended coverage area between panels 3L and 3R and 10. The same applies for garment 300 below.

As shown in FIG. 2A, center seam 214 is approximately positioned along the center of the garment, e.g. along the user's spine and along center axis A of the back side of garment 200. Garment 200 is substantially symmetrical about the central seam 214. Left and right back waist sub-portions 7L and 7R of waist portion 7 are connected to left and right mid shoulder panels 3L and 3R, respectively, generating a garment that has limited stretch from a user's front shoulder region, over the top of the shoulders and downward along the back shoulder region towards the spine, e.g. toward the center seam 214. Portions 7R and 7L connect with panels 3L and 3R, respectively, over a region proximate to a user's shoulder blade.

Figure 2C:
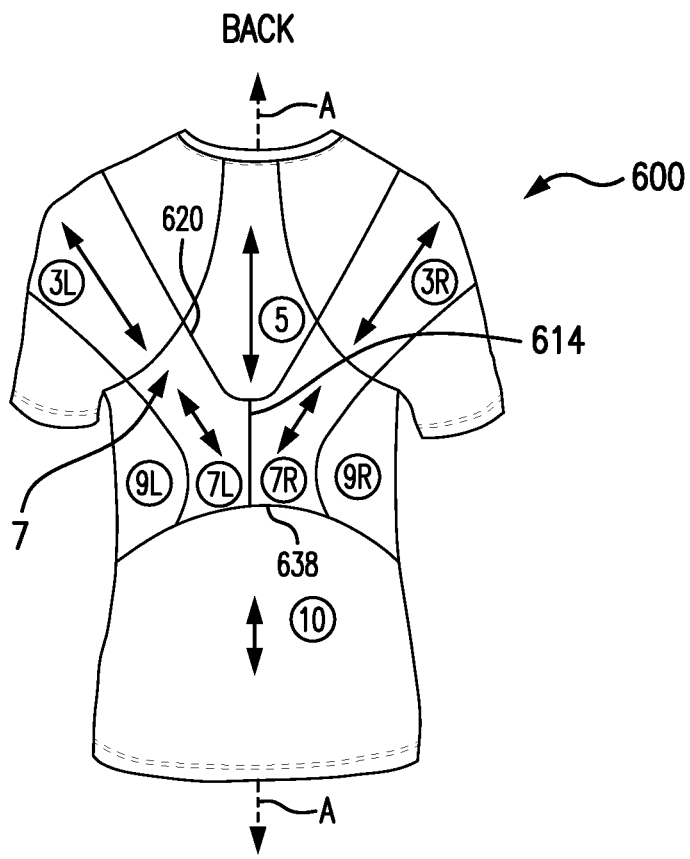
FIG. 2C is a perspective view of an alternative embodiment of the garment of FIG. 2A, showing right and left hand waist portions as separate panels connected by a center seam and schematically showing the grain direction of the fabric for the right and left hand waist portions with double-headed arrows.

As shown in FIG. 2C, a garment 600 is shown. Garment 600 is the same as garment 200 except that instead of a unitarily formed back panel, e.g. back panel 30 of garment 200, upper back portion 5 and a waist panel portion 7 are separate panels from one another held together at seam 620. Additionally, waist panel 7 of garment 600 includes two separate waist sub-panels 7R and 7L held together at seam 614, instead of two separate portions that are from a single unitarily formed panel. Seam 620, described in more detail below, holds panel 5, 7R and 7L together. In FIG. 2C, center seam 614 provides a connection between panels 7L and 7R and serves as the connection of the performance panels 3L and 3R and panels 2L and 2R. Because panels 7R and 7L are two separate panels, the fabric can be cut such the grain of the fabric is parallel to the longitudinal direction of the panel itself, as indicated schematically by the double headed arrows on panels 7L and 7R of FIG. 2C, as opposed to parallel to the center axis A of the garment 600. The grain of the fabric for panel 5 remains generally aligned with the axis A of garment 600, as indicated schematically by the double headed arrow on panel 5 in FIG. 2C. Additionally, in garment 600, panels 7L and 7R are connected to panel 10 with a single seam 638 and to panel 5 with a single continuous seam 620. Panels 9L and 9R are similarly connected to panel 10 along the same single seam 638.

Figure 4C:
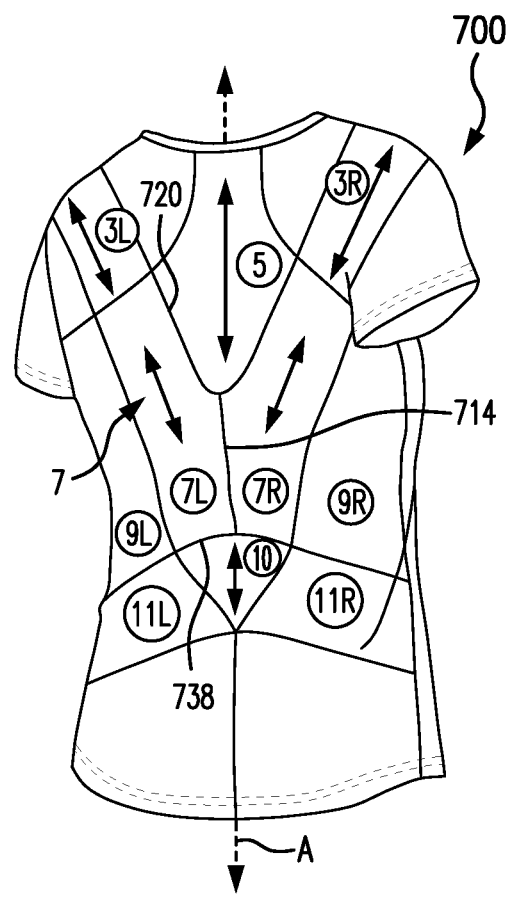
FIG. 4C is a perspective view of an alternative embodiment of the garment of FIG. 4A, showing panels the left and right hand side waist panels as separate panels connected by a center seam and schematically showing the grain direction of the fabric for the left and right hand side waist panels.
Figure 4B:
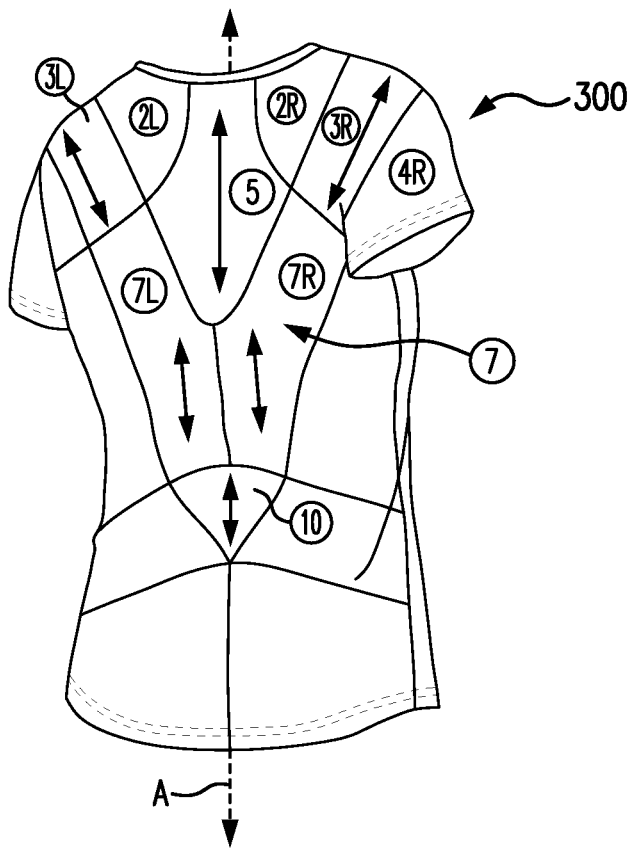
FIG. 4B is a perspective view of the garment of FIG. 4A, schematically showing the grain direction of the fabric for panels left and right hand mid-shoulder panels, upper back panel, left and right hand side waist portions, and the lower back panel.

As shown in FIG. 4C, a garment 700 is shown. Garment 700 is the same as garment 300 except that instead of a unitarily formed central back panel, e.g. back panel 30 of garment 300, upper back portion 5 and a waist panel portion 7 are separate panels from one another held together at seam 720. Additionally, waist panel 7 of garment 700 includes two separate waist sub-panels 7R and 7L held together at seam 714, instead of two separate portions that are unitarily formed as one panel. In FIG. 4C, center seam 714 provides a connection between panels 7L and 7R and serves as the connection of the performance panels 3L and 3R and panels 2L and 2R. By connecting panels 7L and 7R to respective panels 3L and 3R, the pulling force is translated to panels 3L and 3R and up and over each shoulder of a user, thereby pulling back and supporting the shoulders, improving shoulder position and encouraging healthy posture, similar to garments 200 and 300. Panel 7 also provides support for the middle back of the wearer. Because panels 7R and 7L are two separate panels, the fabric can be cut such the grain of the fabric is parallel to the longitudinal direction of the panel itself, as indicated schematically by the double headed arrows on panels 7L and 7R of FIG. 4C, as opposed to parallel to the center axis A of the garment 700. Additionally, in garment 700, panels 7L and 7R are connected to panel 10 with a single seam 738 and to panel 5 with a single continuous seam 720. Seam 738 is also the same continuous seam that connects panels 9R and 11R and panels 9L and 11L.

With reference now to FIGS. 2A-2B, central back panel 30 (and therefore upper back portion 5) includes two fabric layers, e.g. is two fabric plies thick, and is connected to right upper sleeve panel 2R along a first upper back panel seam 216. Right upper sleeve panel 2R includes one fabric layer. Upper back portion 5 is connected to left upper sleeve panel 2L along a second upper back panel seam 218, opposite from the first. Left upper sleeve panel 2L includes one fabric layer. Back panel seam 220 acts as the dividing line for upper back portion 5 and back waist portion 7 of central back panel 30, but because back portion 5 and waist portion 7 are already together as part of the same single panel 30 the seam 220 is a quasi-faux seam as, while there is stitching, it does not actually connect portions 5 and 7 because they are already together. Seam 220 does, however, connect the two fabric layers (in a direction in and out of the page as oriented in FIG. 2A) to keep the two layers of panel 30 from moving relative to one another. In accordance with some embodiments, upper back portion 5 and portion 7 can be two separate panels (in the plane of the paper as viewed in FIG. 2) instead of being unitarily formed with one another, such that seam 220 is needed to connect portions 5 and 7. Each separately formed panel 5 and 7 would also include two layers of material (e.g. would be two plies thick), similar to how upper back portion 5 and back waist portion 7 are when they are unitarily formed with one another. In those embodiments, separate upper back panel 5 would perform a similar function as upper back portion 5, described herein, and back waist panel 7 and its respective sub-portions or sub-panels 7R and 7L would form a similar function as back waist portion 7.

With continued reference to FIG. 2A, upper back portion 5 is located at the top of the garment proximate to a neck hole 224. Upper back portion 5 starts approximately at neck hole 224 and extends downward along the middle-upper back of the wearer, between the shoulder blades. It starts at the back neck seam and joins with back waist portion 7 and panels 2L and 2R. Upper back portion 5 is the hub for all of performance panels/portions (3L, 3R and 7), serving as the connection point. Upper back portion 5 abuts all four performance panels/portions, two at a vertex 226 on the left hand side and two at a vertex 228 on the right hand side. Upper back portion 5 anchors performance panels/portions (3L, 3R and 7) together and distributes the pulling effect across the upper back and pulls the shoulders back. Performance panels/portions (3L, 3R and 7-7R and 7L) form a "U" or "V" shape. Center seam 214 extends longitudinally between upper back portion 5 and mid lower back panel 10, described below.

With continued reference to FIG. 2A, left and right back side panels 9L and 9R, respectively, are oriented opposite from one another across back waist portion 7. Left back waist portion 7L is connected to left back side panel 9L at a first left side panel seam 230. Right back waist portion 7R is connected to right back side panel 9R at a first right side panel seam 232. Right back side panel 9R and left back side panels 9L each include one fabric layer. Left back side panel 9L is connected to front panel 1 at a second left side panel seam 234. Right back side panel 9R is connected to front panel at a second right side panel seam 236.

As shown in FIG. 2A, a lower back panel 10 is positioned below panels/portions 7R, 7L, 9R and 9L. Lower back panel 10 is connected to each of panels/portions 7, 9R and 9L at a respective back panel seams 238a-238c. In some cases, back panel seams 238a-238c can be a continuous seam. Both front panel 1 and lower back panel 10 include single layers of fabric (e.g. are only one ply of fabric thick) and stretch horizontally, as oriented in FIGS. 1 and 2, to provide moderate compression in order to hold garment 200 down on the body. By holding garment 200 down on the body, the two-layered performance panels/portions 3R, 3L, 7 and 5, are able to perform their specified functions.

As shown in FIGS. 3A-4B, in some embodiments, additional panels can be included to accommodate different shapes. Performance panels/portions (5, 3L, 3R, 7) of FIGS. 3A-3B and 4A-4B are substantially similar to performance panels/portions (5, 3L, 3R, 7) of FIGS. 1A-1B and 2A-2B, such that the description used above, with respect to both construction, operation and function, for performance panels/portions (5, 3L, 3R, and 7) of FIGS. 1-2 readily apply to the performance panels/portions (5, 3L, 3R, and 7) of FIGS. 3A-3B and 4A-4B. Similarly, upper back portion 5 of FIGS. 3A-3B and 4A-4B is substantially similar to upper back portion 5 of FIGS. 1A-1B and 2A-2B, such that the description of the construction, operation and function of upper back portion 5 of FIGS. 1A-1B and 2A-2B can readily be applied to upper back portion 5 of FIGS. 3A-3B and 4A-4B. Moreover, numerals 202-236 of FIGS. 1A-1B and 2A-2B represent the substantially the same items as numerals 302-336 of FIGS. 3A-3B and 4A-4B.

Figure 1B:
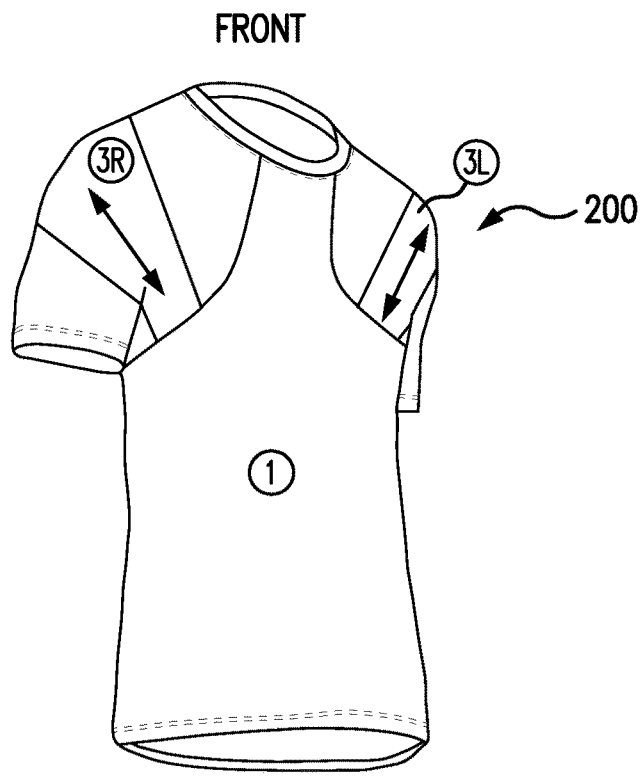
FIG. 1B is a perspective view of the garment of FIG. 1A, schematically showing the grain direction of the fabric for some of the panels with double-headed arrows.
Figure 3B:
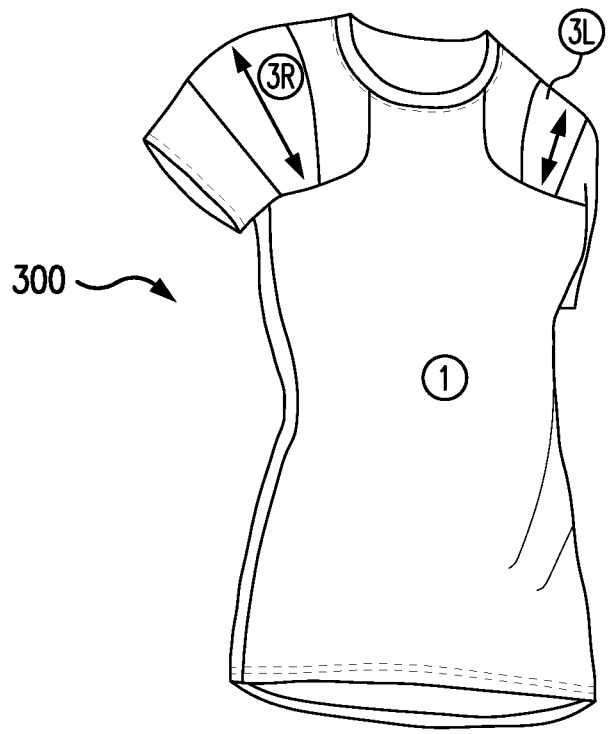
FIG. 3B is a perspective view of the garment of FIG. 3A, schematically showing the grain direction of the fabric for right and left hand mid-shoulder/sleeve panels with double-headed arrows.

With reference now to FIGS. 3A-3B, a front panel 1 largely makes up the front/anterior portion of the garment and is connected to a plurality of shoulder/sleeve panels, similar to front panel 1 of FIG. 1A-1B. The description provided for garment 200 with respect to front panel 1, upper sleeve panels 2R and 2L, mid shoulder panels 3R and 3L, sleeve panels 4R and 4L, and the respective seams therebetween, readily applies to garment 300 and its panels 1, 2R and 2L, 3R and 3L, and 4R and 4L. The seam numbering 202-212 of FIGS. 1A-1B readily corresponds to the same seams 302-312 as shown in FIGS. 3A-3B. Panels 3R and 3L of garment 300, as shown schematically by double headed arrows in FIG. 3B, are similarly cut with the grain like panels 3R and 3L of garment 200.

As shown in FIG. 4A, lower back panel 10 of garment 300 varies from lower back panel 10 of garment 200. Lower back panel 10 in garment 300 is located at the small of the lower back of the wearer and has a v-shaped lower edge, defined by seams 340a and 340b. Portion 7 of central back panel 30, which includes left and right back waist sub-portions 7L and 7R, respectively, is connected to a top edge of panel 10 at seam 344. A seam portion 344a is between back waist portion 7L and panel 10 and a seam portion 344b is between back waist portion 7R and panel 10. In the embodiment of FIGS. 3A-4C, panel 10 includes two layers of fabric (e.g. is two plies thick) and serves as an anchor for left and right back waist portions 7L and 7R allowing portion 7 to provide significant pulling effect. Panel 10 is also cut with the grain, as shown schematically in FIG. 4B by the double headed arrow. Panel 10 of garment 300 also provides targeted compression to the lower back. Center seam 314 of garment 300 is similar to center seam 214 of garment 200. In embodiments where central back panel includes two separate panels 5, and 7 and where waist panel 7 includes two separate panels 7R and 7L instead of two separate portions, e.g. like that of FIG. 4C, center seam 714 provides a connection between panels 7L and 7R serves as the connection of the performance panels (5, 3L and 3R). In those embodiments, panels 7L and 7R would each include two layers of fabric, e.g. would be two plies thick.

As shown in FIGS. 3A-4B, panel 10 of garment 300 is connected to a mid lower back left side panel 11L and a mid lower back right side panel 11R at respective seams 340a and 340b. Panels 11R and 11L both include one fabric layer.

A bottom left side panel 13L is connected at a top seam 342*a* to mid lower back left side panel 11L. A bottom right side panel 13R (opposite from 13L) is connected at a top seam 342*b* to mid lower back left side panel 11R. Bottom right and left side panels 13R and 13L each include one fabric layer and are connected to one another along seam 346. Panels 11R, 11L, 13L and 13R all stretch more (e.g. provide less compression) than performance portions/panels 3R, 3L, 7L, 7R, 5 and 10 of garment 300, while still providing moderate compression holding down garment 300 on the body. This holding down allows all of the 2-layered panels/portions 3R, 3L, 7, 5 and 10 of garment 300 to perform the specified support and lifting functions.

As shown in FIG. 4A, portion 7 is connected to right mid shoulder panel 3R at a respective seam 340*a* and portion 7 is connected to left mid shoulder panel 3L at a respective seam 340*b*. Connection between portion 7 and right and left mid shoulder panels 3R and 3L respectively, are very similar to those described above with respect to garment 200.

Figure 5A:
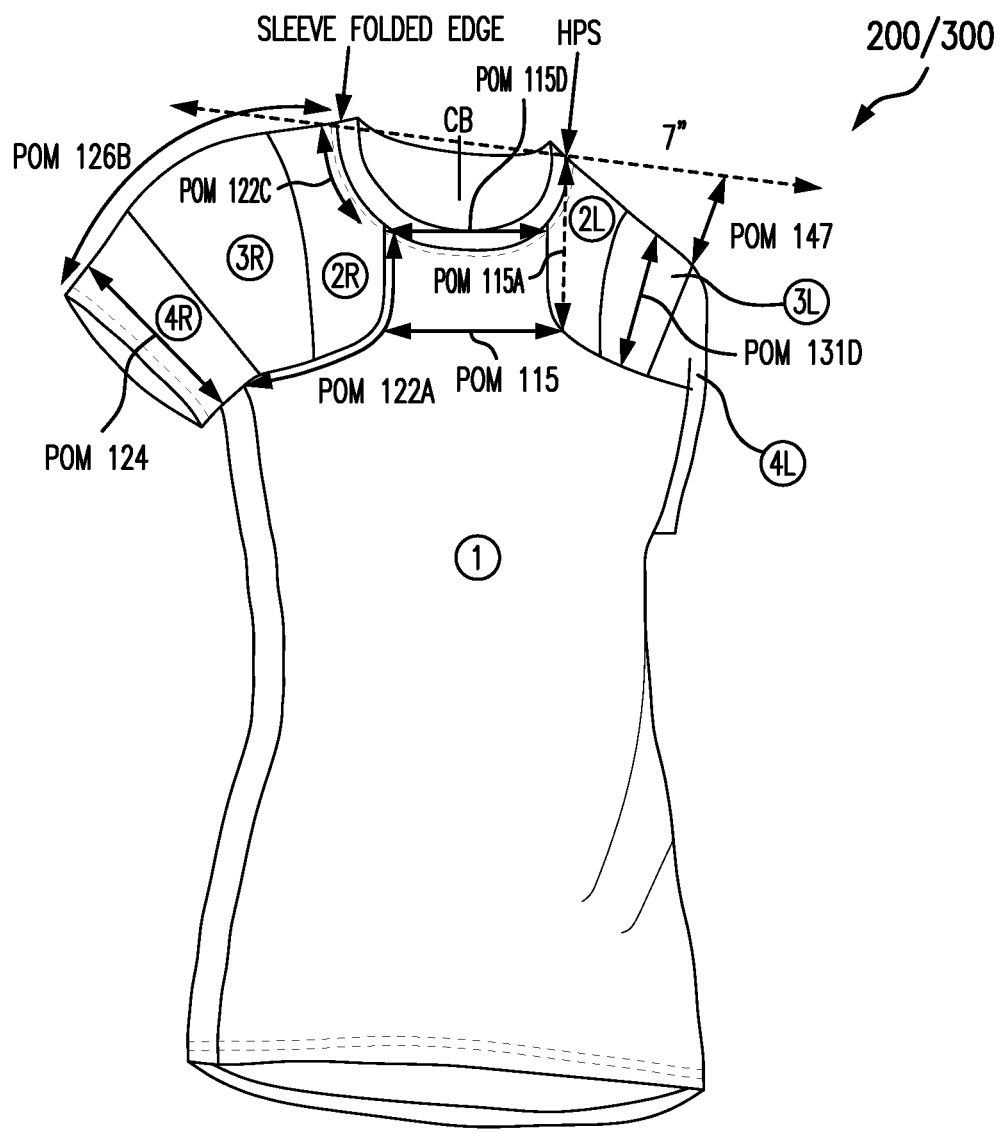
FIGS. 5A-5B is a perspective view of the garment of FIG. 3A, showing measurement points on the front side of the garment.
Figure 5B:
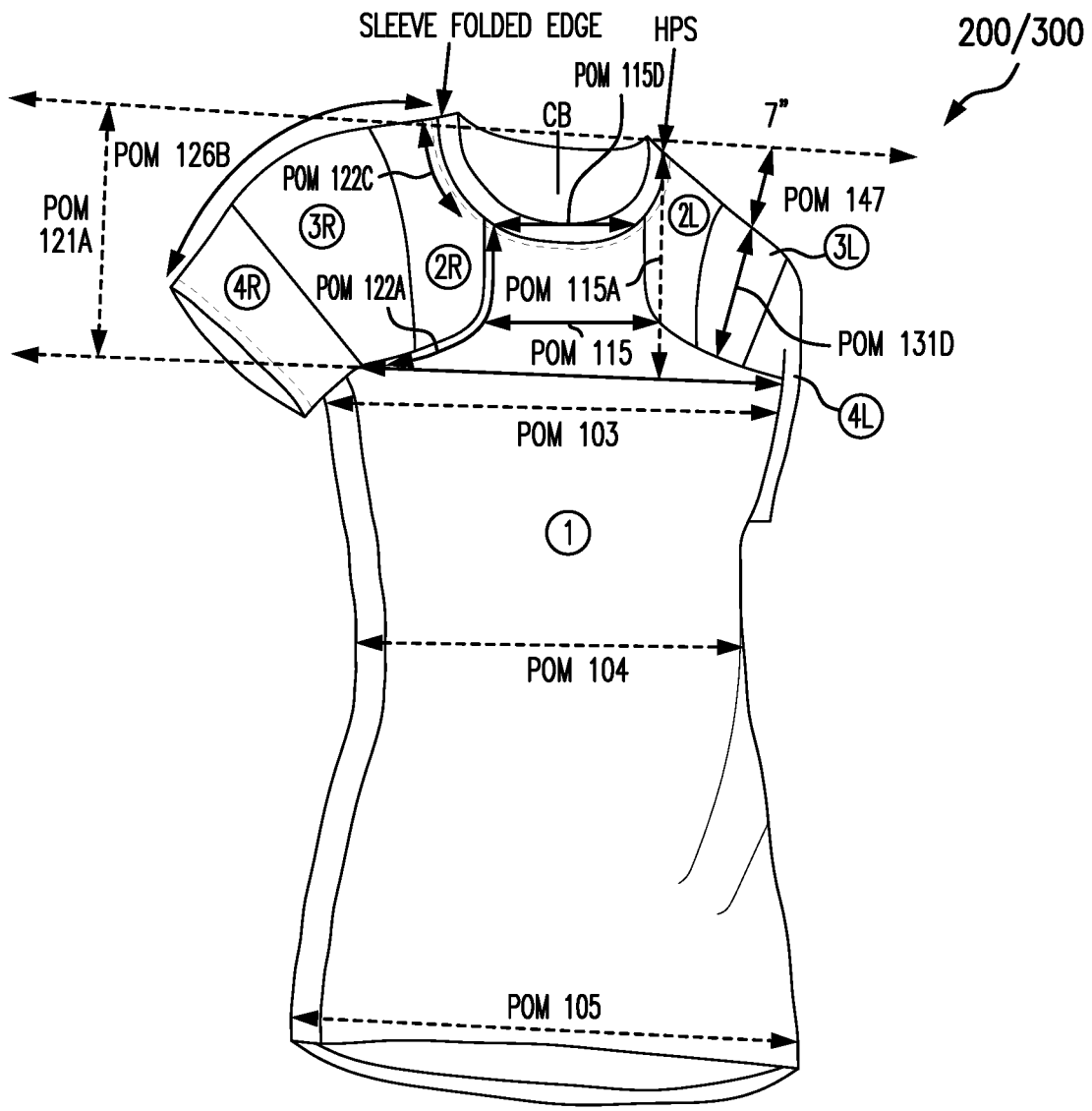
Figure 6A:
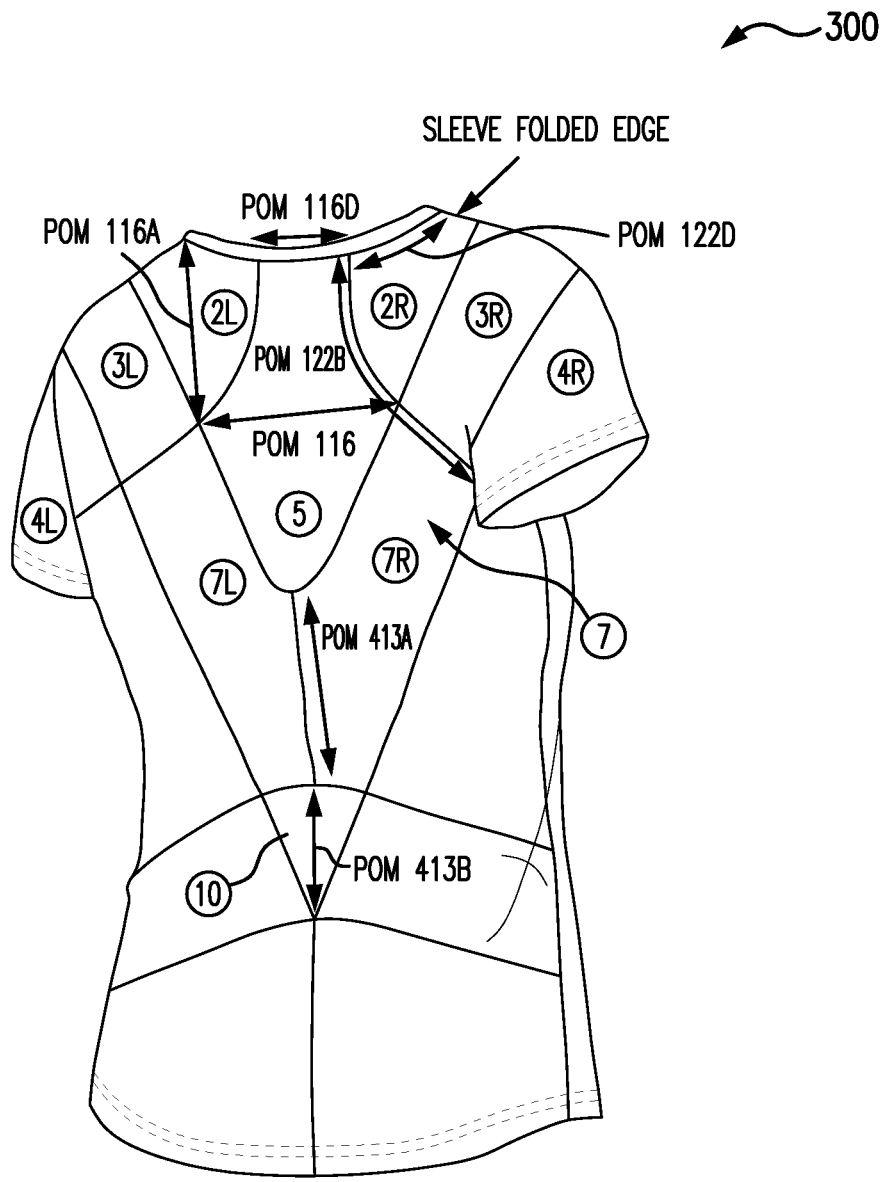
FIGS. 6A-6B is a perspective view of the garment of FIG. 3A, showing measurement points on the back side of the garment.
Figure 6B:
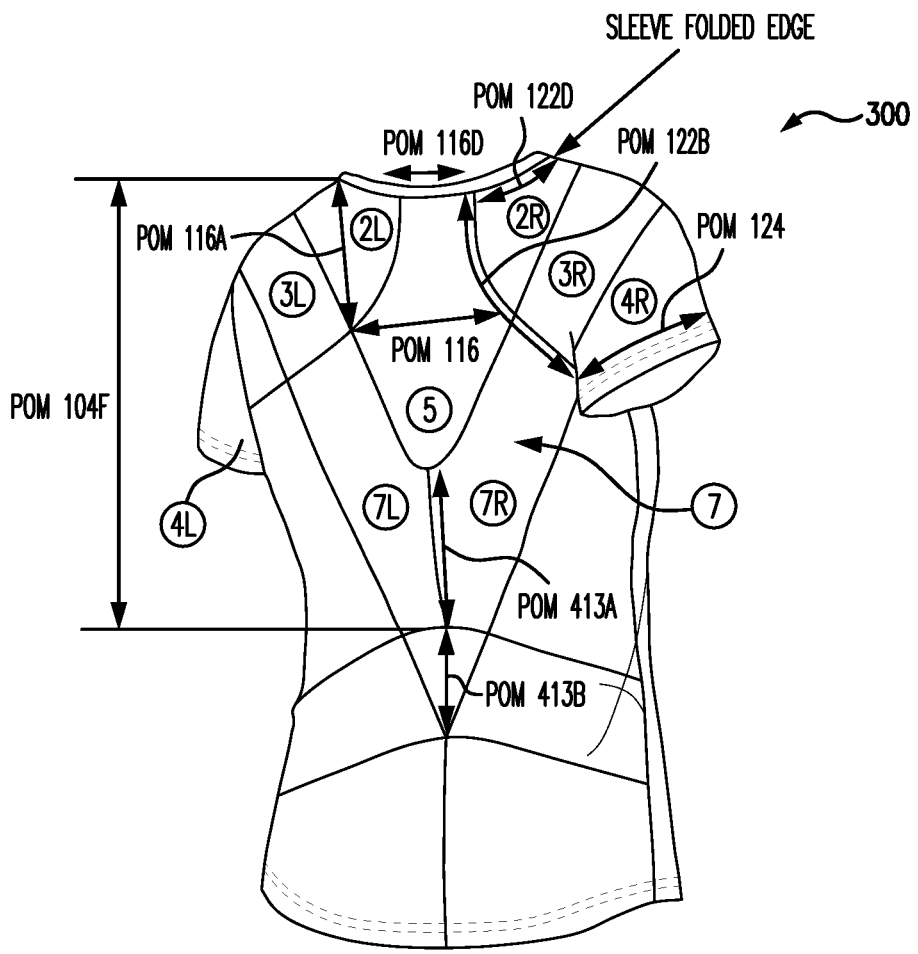
Figure 7:
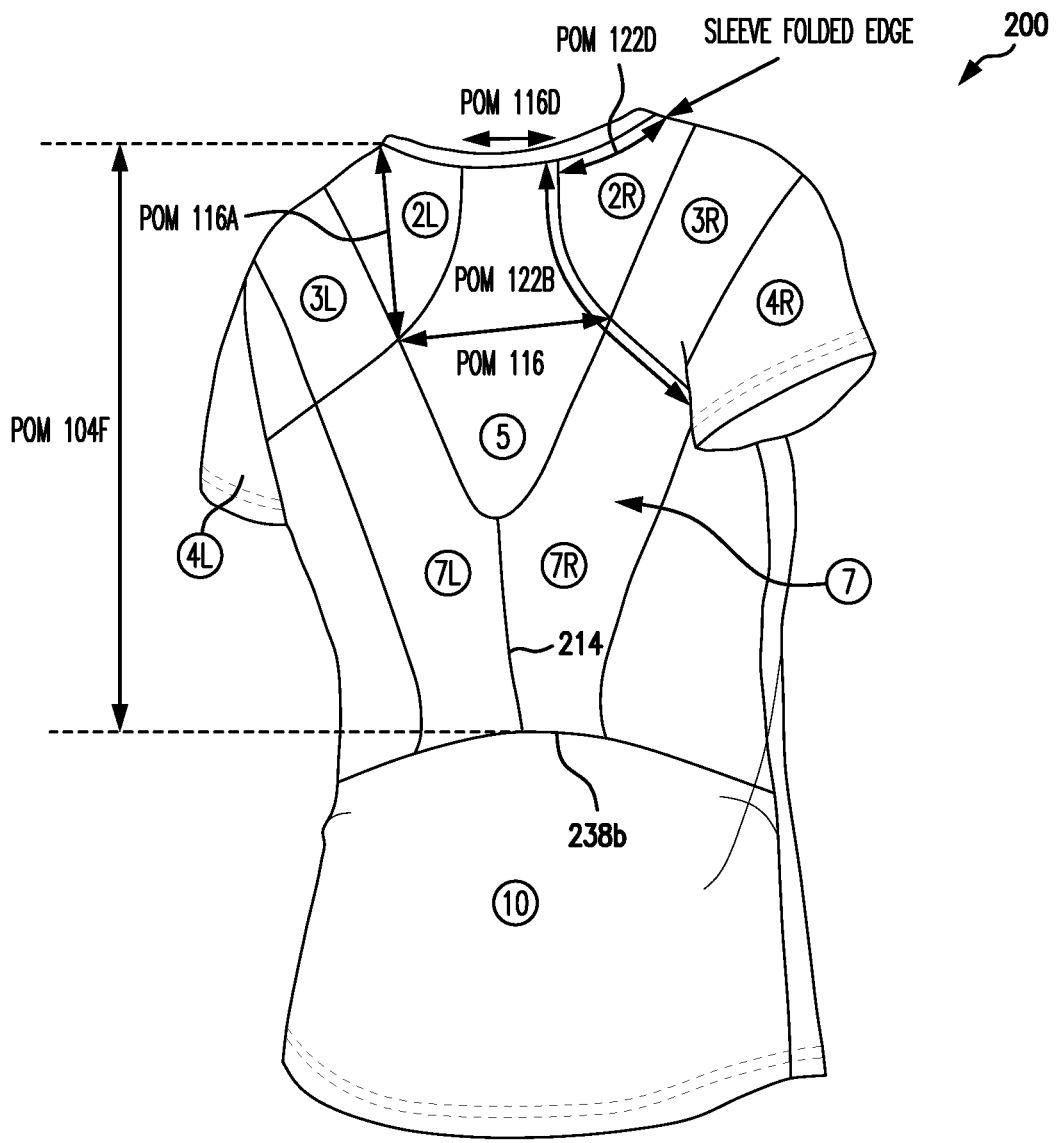
FIG. 7 is a perspective view of the garment of FIG. 1, showing measurement points on the back side of the garment.

As shown in FIGS. 5A-7, garments 200 and 300 are shown with point of measurement (POM) lines shown. POM lines indicate where particular measurements should be taken from. FIG. 5A represents the POMs for both garments 200 and 300, as they are substantially similar from the front. The POMs and their associated dimensions correspond to the garment when at rest, not as stretched on a user. FIG. 6A-6B represents the POMs for the back of garment 300 and FIG. 7 represents the POMs for the back of garment 200. The "width" of POMs 103/104/and 105 are half of the circumferential measurement. In other words, the garment is to be measured in halves.

As shown in FIG. 5B, POM 103 refers to the width at the top of panel 1 (for either garment 200 or 300). POM 103 is measured across the middle of the chest, approximately 1" below the armpit and should be approximately 12-22 inches to create horizontal compression around the wearer. The exact distance depends on the size of the garment (e.g. small, medium, large) and the gender of the garment (e.g. for men or for women). POM 104 refers to the width at the middle of panel 1 at the smallest part of the torso (for either garment 200 or 300). The narrowest width should be approximately 10-21 inches to create horizontal compression around the wearer. The exact distance depends on the size of the garment (e.g. small, medium, large) and the gender of the garment (e.g. for men or for women). POM 105 refers to the width at the bottom of panel 1. At the hip (for either garment 200 or 300), POM 105 for panel 1 should be approximately 14-23 inches to create horizontal compression around the wearer. The proper dimensions for POMs 103, 104, 105 helps to hold the garment in place on the body and allows 3L, 3R and 7 to perform their specified functions.

With continued reference to FIGS. 5A-5B, POM 124 refers to the width of panels 4L and 4R taken 1 inch away from the armpit up to the top of the garment (e.g. garments 200 or 300). The "width" of the panel refers to a half of the circumference of the sleeve. The measurement should be taken in parallel with the sleeve opening of the shirt. POM 124 should be approximately 3-10 inches to create horizontal compression around the top of the arm. The proper dimension for POM 124 helps to hold the garment in place on the body and allows 3L, and 3R to perform their specified functions. POM 121A refers to the armhole depth for either garment 200 or 300. In other words, the distance from the highest point of the shoulder (HPS) to the lowest intersection point between panel 1 and one of panels 4R or 4L. This intersection generally occurs in the armpit region of the wearer. POM 121A should be 6-12 inches. This measurement assists in developing the framework/template for where the performance panels/portions (3L, 3R and 7) should be and therefore will have the ability to perform their specified functions.

With continued reference to FIG. 5A-5B, POM 147 is the vertical distance between the highest point of the shoulder (HPS) to the lowest point of the shoulder (for either garment 200 or 300). In accordance with some embodiments, POM 147 should be approximately 1.5-3 inches from a straight line (drawn approximately parallel to the floor) extending out from the shoulder to the lowest point of the shoulder. The angle between the dashed line of FIG. 5A and the top edge of the shoulder will vary depending on the POM 147 measurement. The proper dimension for POM 147 results in a unique slope of the garment at the shoulder which creates the proper pressure on the shoulder. POM 147 assists in determining where panel 3L and 3R begin.

With continued reference to FIG. 5A-5B, POM 131D for both panels 3L and 3R is the distance between a respective top shoulder portion to the front portion of panels 3L and 3R where they meet with front panel 1 at seam 204 (shown in FIG. 1A). While POM 131D is shown in FIGS. 5A-5B for panel 3L, it will readily be appreciated that a similar POM 131 can be used for panel 3R. POM 131D may range from 2.5-8 inches. POM 131 partially determines how long panels 3R and 3L should be for the pulling back of the shoulders to occur from panels 3L, 3R and 7.

As shown in FIG. 6A-6B, POM 104F for garment 300 refers to the high hip level of the garment. This measurement is taken between the highest point of the shoulder to the center back where seams 342*a*, 342*b* and 346 intersect. POM 104F should be approximately 15-22 inches. POM 104 determines where panels 3L, 3R, 7 end. This measurement governs the length of performance panels/portions (3L, 3R, 7), which enables these panels to perform their specified functions of pulling the shoulders back supporting healthy posture.

As shown in FIG. 7, measurement specification 104F for garment 200 refers to the high hip level of the garment. This measurement is taken between the highest point of the shoulder to the center back where seam 214 intersects seam 238*b*. The POM 104F should be approximately 15 to 22 inches which determines where panels/portions 3L, 3R, 7 end. This is measurement governs the length of performance panels/portions (3L, 3R, 7), which enables these panels to perform their specified functions of pulling the shoulders back supporting healthy posture.

Figure 8:
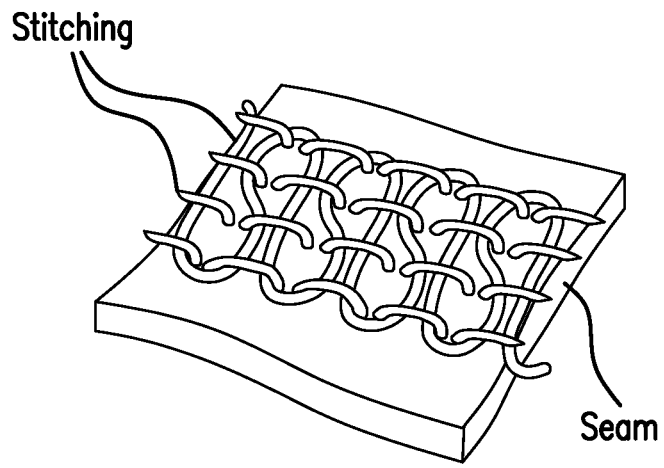
FIG. 8 is a schematic perspective view of a flatlock seam with flatlock stitching.
Figure 9A:
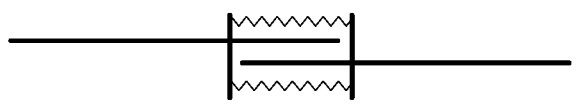
FIGS. 9A-9B are schematic cross-sectional views of seams on the garments of FIGS. 1A-7, showing the material layers overlapped at the seam.
Figure 9B:
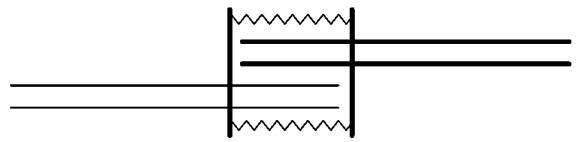
Figure 10B:
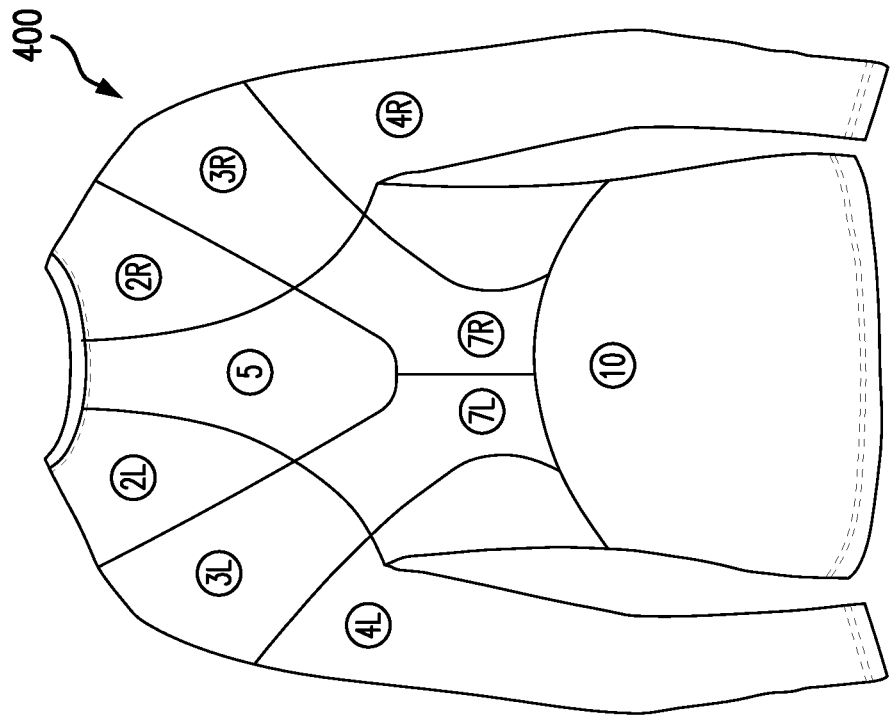
FIG. 10B is a perspective view of the garment of FIG. 10A, showing the garment from a back side.
Figure 10A:
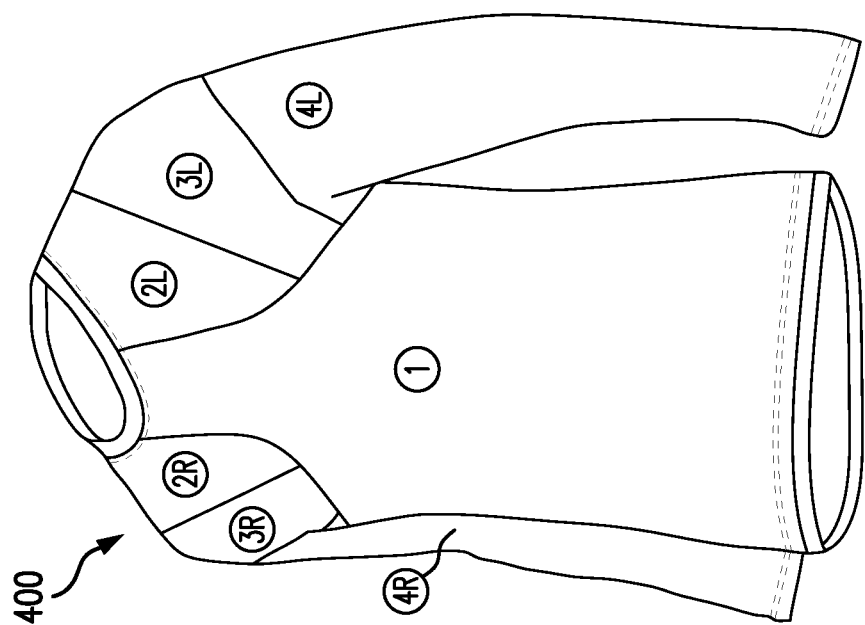
FIG. 10A is another embodiment of a garment for an upper torso portion constructed in accordance with the present disclosure, showing the garment of FIG. 1A with long sleeves from a front side.
Figure 11A:
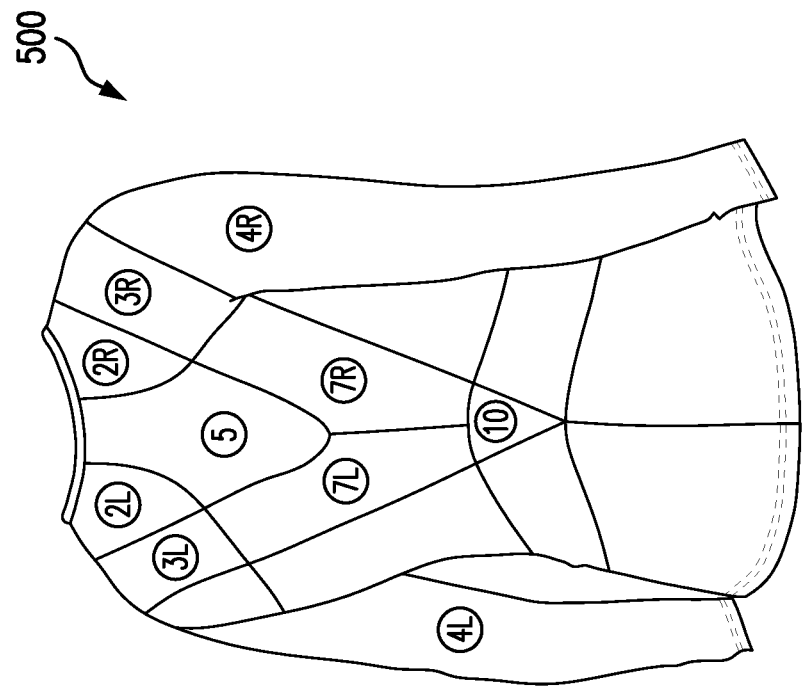
FIG. 11A is another embodiment of a garment for an upper torso portion constructed in accordance with the present disclosure, showing the garment of FIG. 3A with long sleeves from a front side.
Figure 11B:
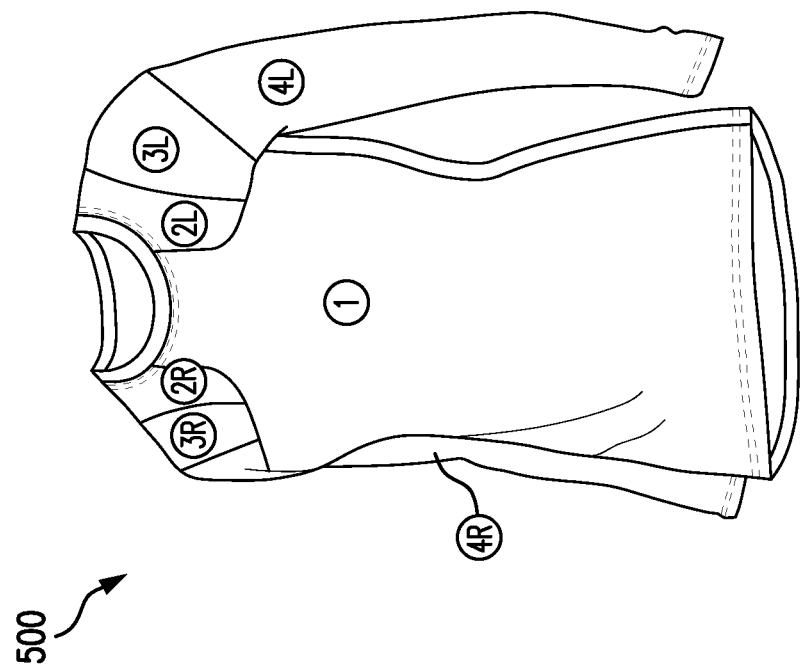
FIG. 11B is a perspective view of the garment of FIG. 11A, showing the garment from a back side.

In the embodiments of FIGS. 1A-7 and 10A-10B, above, seam is used to define the joint between two panels of fabric. It will be readily appreciated that the same line of stitching can be used along one or more seams, or each seam can include its own respective line of stitching. In other words, even though, for example, even though seams 216 and 240*a* are described as being separate seams, those skilled in the art will readily appreciate that seams 216 and 240*a* can readily be a continuous seam. Moreover, it is contemplated that in the embodiments of FIGS. 1A-7 and 10A-10B, the seams used between panels are flat lock seams. Flat lock seams greatly reduce the bulk of the garment, as compared to traditional merrow stitch plus a cover stitch. Flat lock stitching is shown in FIG. 8. The overlap of both the layers of material and the stitching at the seam is minimal when using a flatlock stitch, see, e.g. FIG. 9A, where the layers of overlapping fabric is two. In the case of the shoulder shirt, due to two layer panels, by using a flat lock seam, three to four layers of fabric may result, see, e.g. FIG. 9B. Traditional seaming would potentially cause a buildup of between 6-8 layers of fabric which would cause the shirt to be very uncomfortable.

Those skilled in the art will readily appreciate that a variety of spandex or elastomeric stretch fabrics can be used, such as Lycra® available from INVISTA S.á.r.l., 4123 East 37th Street North, Wichita, Kansas. For example, the material can include 86% Nylon 14% LYCRA® fiber stretch fabric (or another type of spandex fabric). The fabric can have a variety of suitable strengths and elasticities. For example, for garments 200, 300, 400, 500, 600 and 700 when assembled, performance panels/portions 3L, 3R, 7L, 7R have a modulus of elasticity ranging from 3-10 lbf. Panel/portion 5 that serves as the hub for the performance panels a modulus of elasticity ranging from 2-8 lbf. All other panels, 4L, 4R, 2L, 2R, 9R, 9L, 10, 11R, 11L, 13R and 13L all have a modulus of elasticity ranging from 1-5 lbf. (lbf=pounds of force). Each panel can be made from the same material and/or different materials can be used for different panels. For the embodiments described herein, the fabric used for each panel can have the same modulus of elasticity or can vary. The dimensions described above with respect to POMs can also vary on the garment size and type (e.g. men's, women's, kid's).

The methods and systems of the present disclosure, as described above and shown in the drawings, provide for upper torso garments, such as shirts, with superior properties including improved posture and shoulder support. While the apparatus and methods of the subject disclosure have been shown and described with reference to preferred embodiments, those skilled in the art will readily appreciate that changes and/or modifications may be made thereto without departing from the scope of the subject disclosure.

The invention claimed is:

1. A garment comprising:
 a plurality of panels connected to one another at respective seams, the plurality of panels including:
  a front panel;
  a center back section opposite from the front panel, wherein the center back section defines a center panel axis that is co-axial with a center axis of the garment;
  a first shoulder panel extending between the front panel and the center back section and a second shoulder panel extending between the front panel and the center back section, wherein the first shoulder panel and the second shoulder panel are each configured and adapted to extend from the front panel over a respective shoulder of a wearer to the center back section to support and pull back the wearer's shoulders,
 wherein the center back section includes a unitary central back panel having an upper back portion and a waist portion, wherein the waist portion includes a first sub-portion and a second sub-portion, wherein the first sub-portion of the waist portion includes a first top edge that abuts and connects to a bottom edge of the first shoulder panel and wherein the second sub-portion of the waist portion includes a second top edge that abuts and connects to a bottom edge of the second shoulder panel such that a pulling force exerted on a wearer by the first and second sub-portions of the waist portion is translated from the first and second sub-portions to the first and second shoulder panels, respectively, to provide targeted compression at a respective shoulder and muscles along a spine and to retract a wearer's shoulder blades,
 wherein a second edge of the first sub-portion and second edge of the second sub-portion of the waist portion meet at a seam defined along the center panel axis, wherein the first and second sub-portions are symmetrical about the center panel axis and abut one another along the center panel axis to form a "v"-shape between the first sub-portion and the second sub-portion within the unitary central back panel, wherein a point of the "v" points downward and away from the first and second shoulder panels.

2. The garment as recited in claim 1, wherein the upper back portion and the waist portion have a first modulus of elasticity and wherein the shoulder panel has a second modulus of elasticity, and wherein the second modulus of elasticity is greater than the first modulus of elasticity.

3. The garment as recited in claim 1, wherein the waist portion, the upper back portion and the first and second shoulder panels have moduli of elasticity greater than remaining portions of the garment.

4. The garment as recited in claim 1, wherein the respective seam connecting the waist portion and the respective shoulder panels are configured to be proximate to a shoulder blade region of a wearer.

5. The garment as recited in claim 1, wherein the central back panel includes two layers of fabric.

6. The garment as recited in claim 1, wherein the plurality of panels includes a lower back panel connected to a lower edge of the center back section, wherein the lower back panel extends from the lower edge of the center back section to a bottom seam of the garment.

7. The garment as recited in claim 1, wherein the shoulder panel is cut approximately 8-14% shorter than an intended coverage area such that the shoulder panel is configured and adapted to stretch when worn and assist in lifting and pulling back of at least one shoulder.

8. The garment as recited in claim 1, wherein a fabric grain of the upper back portion of the center back section is aligned with the center panel axis.

9. The garment as recited in claim 8, wherein a fabric grain of the first and second shoulder panels is angled with respect to the center panel axis, and wherein a fabric grain of the waist portion is angled with respect to the center panel axis, wherein the fabric grain of the first shoulder panel and the fabric grain of the first sub-portion of the waist portion are angled with respect to the center panel axis in a common first direction, and wherein the fabric grain of the second shoulder panel and the fabric grain of the second sub-portion of the waist portion are angled with respect to the center panel axis in a second common direction, wherein the first common direction is different from the second common direction.

10. The garment as recited in claim 1, wherein at least one of the center back section or the shoulder panel include two layers of fabric.

11. The garment as recited in claim 1, wherein the first shoulder panel and the second shoulder panel each extend in a posterior direction from the front panel to the center back section.

\* \* \* \* \*